United States Patent [19]

Burnham

[11] 4,024,202
[45] May 17, 1977

[54] OLIGOMERISATION PROCESS

[75] Inventor: David Robert Burnham, Runcorn, England

[73] Assignee: Imperial Chemical Industries Limited, London, England

[22] Filed: May 28, 1975

[21] Appl. No.: 581,482

[30] Foreign Application Priority Data

June 6, 1974 United Kingdom ............ 25094/74

[52] U.S. Cl. .................. 260/683.15 D; 260/439 R
[51] Int. Cl.$^2$ .......................................... C07C 3/10
[58] Field of Search ........................... 260/683.15 D

[56] References Cited

UNITED STATES PATENTS

| 3,647,915 | 3/1972 | Bauer et al. | 260/683.15 D |
| 3,686,159 | 8/1972 | Bauer et al. | 260/683.15 D |
| 3,736,264 | 5/1973 | Chauvin | 260/683.15 D |

*Primary Examiner*—C. Davis
*Attorney, Agent, or Firm*—Cushman, Darby & Cushman

[57] ABSTRACT

Process for the oligomerisation of ethylene to give a high proportion of $C_4$-$C_8$ oligomers of which a high proportion (>80%) are α-olefins, using, as catalyst a Group VIII metal hydrocarbyl compound supported on an inorganic oxide which has surface hydroxyl groups with which the compound will react. Nickel is the preferred Group VIII metal.

11 Claims, No Drawings

OLIGOMERISATION PROCESS

This invention relates to the oligomerisation of ethylene and, especially, to its oligomerisation to predominantly α-oligomers.

Processes for the oligomerisation of ethylene using Group VIII metal catalysts, especially processes which give rise to low molecular weight oligomers having a preponderance of α-olefins, generally make use of homogeneous catalysts which may be difficult to separate from the oligomeric products. Heterogeneous catalysts have also been proposed for this purpose, and while these are more readily separated from the products, they have tended to be those which give rise to the highest activity and usually have low selectivity to α-olefins and vice versa.

We have now found that certain supported Group VIII metal hydrocarbyl catalysts enable ethylene to be oligomerised heterogeneously with high activity while giving high selectivity to α-olefins.

According to the present invention, a process for the oligomerisation of ethylene comprises contacting the ethylene with a compound of a metal of Group VIII of the Periodic Table of the Elements supported on an inorganic particulate material having a hydroxylic surface substantially free from adsorbed moisture, the said compound being one having two hydrocarbyl or substituted hydrocarbyl groups bonded to the metal, one of said groups being capable of reacting with the hydroxylic surface of the support.

Preferred Group VIII metals are those of the first row of the Periodic Table of the Elements, e.g. cobalt and nickel; but nickel is an especially preferred metal.

(All references to the Periodic Table are to the version of the Periodic Table of the Elements printed inside the back cover of "Advanced Inorganic Chemistry" by F A Cotton and G Wilkinson, 2nd Edition, Interscience Publishers, 1966).

Suitable hydrocarbyl or substituted hydrocarbyl groups include alkyl and alkenyl (including π-allyl) groups and substituted alkyl groups of formula —$CH_2Y$ where Y is an aromatic or polyaromatic group, such as phenyl or naphthyl, or ring-substituted derivatives thereof or a group of formula $Z(R^1)_3$ where Z represents carbon, silicon, germanium, tin or lead, preferably silicon, and each $R^1$ represents a hydrocarbyl group or a hydrogen atom. Examples of such substituted alkyl groups include benzyl, neo-pentyl and trimethyl silylmethyl. Group VIII metal complexes which are specifically excluded from the above definition are those in which two hydrocarbyl ligands are π-bonded to the metal and the total number of centers on the ligands involved in the π-bonding exceeds 6, for example, dicyclopentadienylnickel.

The Group VIII metal compounds may also contain other groups or ligands co-ordinated with the metal in order to satisfy the valency and/or co-ordination requirements of the metal. Groups which act as Lewis bases are especially useful. Examples of such groups include phosphines, amines, pyridine, bypyridyl and sulphur-containing groups, such as thioxanthene and the di-alkylsulphides. Some of these groups may have a beneficial effect in that they may stabilise the catalyst and/or its precursors or they may serve to modify the selectivity of the catalyst. Organic phosphines, e.g. those of formula $PR_3$, where each group R, which may be the same or different, is a hydrocarbyl group, are especially useful in these respects. The Lewis base may be added in excess, but the ratio of, e.g., phosphine to nickel, should not generally exceed 3/1.

The inorganic particulate support may comprise any substantially inert metal oxide or related compound, e.g. a phosphate, having a hydroxylic surface with which one hydrocarbyl group of the said Group VIII metal compound may react with the elimination of the free hydrocarbon equivalent to the reacting hydrocarbyl group. By the term "hydroxylic surface" we mean a plurality of —OH groups attached to the surface of the particulate material, the hydrogen atom of the —OH group being capable of acting as a proton source, that is, having an acidic function. It will be appreciated that such a material, although substantially inert to ethylene and the oligomeric products of the reaction, may react with the Group VIII metal compound in the manner described above.

Examples of suitable materials having hydroxylic surfaces include γ-alumina, silica, aluminium phosphate and zirconium phosphate. A particularly preferred material is γ-alumina.

It will be appreciated that not all Group VIII metal compounds falling within our definition will necessarily react with all such particulate support materials, since all hydrocarbyl groups do not possess the same reactivity towards the —OH groups of all such supports. However, the relative reactivity of the hydrocarbyl groups bonded to the metal with the —OH groups of the chosen support may be ascertained by simple experiment.

For example, Group VIII metal compounds having one hydrocarbyl ligand which is very reactive towards the support and one which remains attached to the metal after reaction of the metal compound and support, and is thus capable of initiating the oligomerisation reaction, are particularly useful in the processes of our invention. Examples of such compounds include those in which one hydrocarbyl group is π-bonded and the other is σ-bonded to the metal, e.g., π-crotylnickelmethyl, π-crotylnickelmethyltriphenyl phosphine and π-allylnickelbenzyltri-cyclohexyl phosphine. Without prejudice to the invention, experimental evidence suggests that when such compounds react with, say, alumina, the methyl or benzyl group reacts with the —OH groups of the alumina with elimination of methane or toluene, the π-crotyl or π-allyl group remaining bonded to the nickel atom which is, in turn, bonded to the support via the —O— group of the —OH group which took part in the initial reaction.

As previously mentioned, the support must be free of adsorbed water, as this would merely react with and destroy the Group VIII metal hydrocarbyl compound. The support may be readily freed from such adsorbed water, for example, by a simple thermal treatment. However, calcination at a temperature which would drive off all the —OH groups of the support must be avoided. In general, temperatures in the range 150° to 1000° C have been found to be suitable.

Catalysts for use in our process may be prepared by contacting the support material with a solution of the Group VIII metal compound in a suitable solvent. Solvents which are suitable for this purpose include aromatic and aliphatic hydrocarbons, for example, toluene and hexane. Preferably the support material is slurried in the solvent and a solution of the Group VIII metal compound added slowly to it with continuous stirring until the supernatant liquid indicates the presence of excess of the Group VIII metal compound. The amount of Group VIII metal compound which will react with the support will depend upon the nature of the compound and the support material, but may be readily ascertained by, in effect, titrating a known quantity of the support with the compound to be used, as described above. In general the concentration of Group VIII metal compound will be in the range 0.01 to 0.5 m mole/g of support.

The oligomerisation process of our invention is conveniently performed by contacting a slurry of the catalyst in a hydrocarbon solvent with ethylene under dry, oxygen-free conditions. The ethylene may be in the gaseous phase or dissolved in a suitable solvent, e.g. toluene. Alternatively, the catalyst may be filtered from the slurry, washed with solvent and dried, and then used in a fixed or moving bed over or through which the ethylene may be passed, again in gaseous or liquid phase.

The reaction may be carried out continuously or batchwise at a reaction temperature in the range 0° to 120° C, preferably 10° to 70° C. Reaction pressure is not critical, but pressures up to 50 bars are convenient, although higher pressures may be used if desired. Pressures in the range 20 to 50 bars are particularly preferred.

Using the oligomerisation process of our invention it is possible to obtain mixtures of ethylene oligomers >80% of which are α-olefins and >80% of which have molecular weights $\geq$ 112.

The invention will be illustrated by the following Examples.

EXAMPLE 1

Preparation of π-crotyl nickel methyl tricyclohexyl phosphine

All operations were carried out under dry, oxygen-free conditions, under an atmosphere of nitrogen.

1. Preparation of bis(cyclooctadienyl)nickel 122 g of nickel acetylacetonate (0.44 moles) was azeotroped in 500 ml of toluene until there was no water in the distillate. After filtration, 268 ml of cycloocta 1,5 diene (2.18 moles) and 10 g butadiene (0.19 moles) were added, followed by 61 ml of triethylaluminium (0.45 moles) in 150 ml of toluene at −2° to −5° C over 5 hours. The bright yellow precipitate (72.2 g, 0.26 moles) of bis(cyclo octadienyl)nickel was filtered and washed with toluene.

2. Preparation of π-crotyl nickel bromide

A slurry of bis(cyclo octadienyl)nickel in ether (0.26 moles in 500 ml) maintained at −80° C was added to 43 g of crotyl bromide (0.32 moles) in 200 ml of diethyl ether over 7 hours at −5° to −10° C. The reactants were stirred for a further 7 hours to complete reaction. The ether and cyclo octadiene were then pumped off and the solid π-crotyl nickel bromide redissolved in ether and filtered.

3. Preparation of π-crotyl nickel bromide tricyclohexyl phosphine

Tricyclohexylphosphine (11.2 g, 40 m moles) in 100 ml of diethyl ether at −20° C was added to 40 m mole of π-crotyl nickel bromide in 216 mls of hexane. The orange yellow precipitate was filtered and dried.

The solid had NMR and I.R. spectra consistent with the proposed formula and had the elemental analysis shown below.

|         | C    | H   | Br   | P   | Ni   |
|---------|------|-----|------|-----|------|
| Found:  | 55.4 | 8.4 | 16.6 | 6.5 | 13.4 |
| Theory: | 55.5 | 8.5 | 16.8 | 6.5 | 12.5 |

4. Preparation of π-crotyl nickel methyl tricyclohexylphosphine

π-Crotyl nickel bromide tricyclohexylphosphine (29 m mole) was slurried in 200 ml of diethyl ether at −20° C. To this slurry 30 m mole of methyl magnesium chloride in 300 ml of ether was added at −20° C over 8 hours. The resultant yellow solid was filtered and recrystallised from hexane.

NMR analysis showed the complex to contain π-crotyl and nickel methyl groups and elemental analysis showed the complex to be halogen and magnesium free.

Preparation of Supported Catalyst

Grade B γ-alumina (mesh size 20–120 μ) was dried for 2 hours in nitrogen at 500° C and cooled under nitrogen.

π-Crotyl nickel methyl tricyclohexylphosphine complex (2.05 m moles) was dissolved in 20 ml of dry, oxygen free toluene and 3 ml of the resulting solution (0.31 m moles) was added to a slurry of the dried Grade B alumina (4.0 g) in toluene (20 ml) at room temperature. The alumina support material turned brown and the color of the supernatant was discharged.

Oligomerisation procedure 400 mls of dry, oxygen free toluene were added to a 1 liter autoclave which had been previously evacuated for at least 1 hour at a temperature above 100° C. The pressure in the autoclave was brought to just above one atmosphere with dry, oxygen-free ethylene and the temperature adjusted to 22° C. A slurry containing 1 g of the alumina-supported π-crotylnickelmethyltricyclohexylphosphine, prepared as described above, was syringed into the autoclave, the ethylene pressure raised to 35 bars and the temperature adjusted to 26° C. Samples of gas and liquid were taken at intervals throughout the reaction and after 2 hours the reaction was stopped by venting the ethylene. Final samples were taken just before termination of the reaction. Both liquid and gaseous samples were analysed by gas/liquid chromatography (g.l.c.), using ethylene and toluene as internal standards for the gas and liquid samples respectively. The butene yield was obtained from the calculated solubility of butene in the toluene/ethylene mixture.

After one hour, the reaction was found to have yielded

| Butene-1 | 29.3 g |
| Hexene-1 | 0.28 g |
| octene-1 | 0.20 g |
| butene-2 | 0.80 g |
| other oligomers | 1.00 g |

It will thus be seen that the selectivity to α-olefins was 95%, of which more than 99% was $C_4$ to $C_6$ olefins. The total activity, calculated on the production of α-olefins per millimole of Group VIII metal catalyst was 305 g/m mole nickel/hour (hereinafter referred to simply as g/m mole/hour). At termination of reaction the ethylene consumed was >15,000 moles/mole Ni.

COMPARATIVE EXAMPLE A

The procedure of Example 1 was repeated using 0.1 m moles of π-crotyl nickel methyl tricyclohexylphosphine but with no support, at a temperature of 30° C and pressure of 31 bars.

After 1 hour the total activity was found to be only 0.3 g/m mole/hour and selectivity less than 50%.

EXAMPLES 2 to 6

Several oligomerisations were carried out using the catalyst and procedure of Example 1, but varying the reaction temperature. In the case of Example 2, only 150 ml of toluene was used. The results are shown in Table 1 below.

Table 1

| Example No. | Temp ° C | Activity g/m mole/hr | Selectivity to α-olefin (%) | % $C_4$ | % $C_6$ |
|---|---|---|---|---|---|
| 2 | 8 | 160 | 96 | 91 | 8 |
| 3 | 22 | 260 | 96 | 91 | 8 |
| 4 | 45 | 190 | 94 | 91 | 8 |
| 5 | 65 | 110 | 87 | 84 | 15 |
| 6 | 75 | 80 | 85 | 78 | 15 |

EXAMPLE 7

Preparation of π-crotyl nickel methyltriphenylphosphine

The preparation substantially followed that described under Example 1, except for the use of triphenylphosphine in place of tricyclohexylphosphine in stage (3); furthermore, the π-crotyl nickel bromide triphenylphosphine complex was not isolated.

The final complex was not recrystallized from hexane, but was dissolved in toluene after removal of ether. The complex (0.4 m moles) was then allowed to react with Grade B alumina (6 g) in toluene.

Oligomerisation

The general procedure of Example 1 was followed using, as catalyst, 0.067 m moles π-crotyl nickel methyltriphenylphosphine on 1 g alumina, at a temperature of 65° C and pressure of 35 bars.

The activity was 60 g/m mole/hour and selectivity to α-olefins 92%, 85% of which were $C_4$ and 12% $C_6$ olefins.

COMPARATIVE EXAMPLE B

The procedure of Example 7 was repeated; but the complex was unsupported.

Activity was only 0.03 g/m mole/hour and selectivity to α-olefins 65%. No oligomers higher than $C_4$ were detected.

COMPARATIVE EXAMPLE C

Triphenylphosphine (1 m mole) in 2 ml of toluene was added to 0.93 m moles of biscyclopentadienyl nickel in 10 ml of toluene. There was no color change. Part of the resulting solution (1 ml) was added to a toluene slurry containing 2.2 g of Grade B alumina dried as previously described. The alumina became a brown and the color of the solution was discharged.

Oligomerisation of ethylene was carried out at 30° C and 35 bar by the procedure of Example 1. No oligomers were detected.

EXAMPLE 8

Preparation of π-allyl nickel benzyl tricyclohexylphosphine

π-Allyl nickel chloride was prepared by the procedure described for π-crotyl nickel bromide under Example 1, except that allyl chloride was used in place of crotyl bromide. The remainder of the preparation followed closely that in Example 1, except for the use of benzyl magnesium chloride in place of methyl magnesium chloride.

The NMR spectrum of a solution of the solid orange product indicated the presence of π-allyl nickel benzyltricyclohexylphosphine.

Characterizing lines had the following τ values:
5.0 m, 6.75 d, 7.1 d, 7.3 m, 7.7 dd, 7.9–9.0 m and 2.7 m (m = multiplet; d = doublet)

Oligomerisation

The above complex was supported on Grade B alumina and used to oligomerise ethylene by the general procedure of Example 1 at 30° C and a pressure of 31 bars.

The activity was 430 g/m mole/hour and the selectivity to α-olefins was 95%, of which 91% were $C_4$ and 8% $C_6$ olefins.

EXAMPLE 9

Preparation of π-crotyl nickel methyl triisopropylphosphine

The method followed that of Example 1 except for the use of triisopropylphosphine instead of tricyclohexylphosphine.

The NMR spectrum of a solution of the complex indicated the presence of π-crotyl nickel methyl triisopropylphosphine. Characterizing lines had the following τ values.
5.38 m, 7.0 m, 7.15 d, 7.8 m, 8.25 tr, 10.05 d 8.3–9.1 m (tr = triplet)

Oligomerisation

The above complex was supported on Grade B alumina and used to oligomerise ethylene by the general procedure of Example 1 at 40° C and a pressure of 31 bars.

Activity was 210 g/m mole/hour and the selectivity to α-olefins 96%, of which 92% were $C_4$ and 8% $C_6$ olefins.

EXAMPLE 10

Preparation of bis π-allyl nickel

π-allyl nickel chloride is prepared as described under Example 8, and 45 m moles of the product was dissolved in 700 ml of dry, degassed pentane. Degassed water (50 ml) was then added and the solution stirred vigorously until the color changed from deep red to bright yellow. Two layers were allowed to separate, the flask cooled to −20° C, and the dark green aqueous layer was removed. The yellow pentane layer was then treated with a further 50 ml of degassed water. After cooling to −20° C, the aqueous layer was again removed.

The pentane layer contained 0.032 m moles of nickel/ml and no detectable chlorine.

Part of the bis π-allyl nickel (0.29 m moles) was added to 3.3 g of dried Grade B alumina slurried in toluene. The color of the supernatant liquid was discharged and the alumina became orange/brown in color.

Oligomerisation

The above supported catalyst was used to oligomerise ethylene by the general procedure of Example 1 at a temperature of 30° C and pressure of 31 bars.

The activity was 290 g/m mole/hour and the selectivity to α-olefins 85%, of which 93% was $C_4$ and 7% $C_6$ olefins.

EXAMPLE 11

A catalyst comprising π-crotyl nickel methyl tricyclohexylphosphine supported on Grade B alumina was used to oligomerise ethylene using the general procedure of Example 1, at a temperature of 45° C but at various pressures. The effect on the yield of butene-1 is shown in Table 2 below.

Table 2

| Pressure (Bars) | Relative Yield of Butene-1 |
| --- | --- |
| 35 | 1.00 |
| 21 | 075 |
| 7 | 0.37 |

EXAMPLE 12

Catalysts comprising π-crotyl nickel methyl triphenylphosphine supported on Grade B alumina but with varying amounts of phosphine were used to oligomerise ethylene using the general procedure of Example 1 at a temperature of 30° C and a pressure of 35 bars. The effect of excess phosphine on the yield of butene-1 is shown in Table 3 below Table 3

| Ni/P Ratio | Relative Yield of Butene-1 |
| --- | --- |
| 1/1 | 1.00 |
| 1/3 | 0.9 |
| 1/11 | 0.5 |

EXAMPLES 13–15

A π-allyl nickel benzyl tricyclohexylphosphine complex prepared as in Example 8 was reacted with a number of inorganic particulate supports slurried in toluene and the resulting supported catalysts used to oligomerise ethylene using the procedure of Example 1 at a pressure of 31 bars and a temperature of 30° C. The results are shown in Table 4 below.

Table 4

| Example No. | Support | Activity g/m mole/hr | Selectivity to α-olefins | % $C_4$ | % $C_6$ |
| --- | --- | --- | --- | --- | --- |
| 13 | AlPO$_4$ | 780 | 83 | 81 | 18 |
| 14 | Kaolin | 140 | 87 | 82 | 17 |
| 15 | Silica | 2 | 74 | 100 | 0 |

EXAMPLE 16

Preparation of π-crotylnickel methyl 0.37 g (0.48 m moles) of π-crotylnickelbromide, prepared as described in Example 1, was dissolved in toluene and cooled to −80° C. 0.96 m moles of methyl magnesium chloride were then added and the white precipitate which formed was filtered off the temperature being maintained at −80° C. 0.09 m moles of the product were reacted with 1 g of Grade B alumina at −80° C.

Oligomerisation

The above catalyst was used to oligomerise ethylene using the general procedure of Example 1 at a temperature of 65° C and a pressure of 10 bars.

The activity was 17 g/m mole/hour and selectivity to α-olefins 83%, of which 98% was $C_4$ and 2% $C_6$ olefins.

What we claim is:

1. A process for the oligomerisation of ethylene which comprises contacting the ethylene with a compound of a metal of Group VIII of the Periodic Table of the Elements supported on an inorganic particulate material having a hydroxylic surface substantially free from adsorbed moisture, the said compound being one having two hydrocarbyl or substituted hydrocarbyl groups bonded to the metal, one of said groups being capable of reacting with the hydroxylic surface of the support, provided that both of said two hydrocarbyl groups are not π-bonded to said nickel and provided that the total number of centers on the ligands involved in π-bonding does not exceed 6.

2. A process according to claim 1 in which the Group VIII metal is nickel.

3. A process according to claim 1 in which one of the hydrocarbyl groups is π-bonded and the other σ-bonded to the metal.

4. A process according to claim 3 in which the π-bonded group is a π-allyl or a π-crotyl group and the σ-bonded group is a methyl or benzyl group.

5. A process according to claim 3 in which the Group VIII metal compound also contains one or more groups capable of acting as Lewis bases.

6. A process according to claim 5 in which the group capable of acting as a Lewis base is a phosphine of formula PR$_3$ where each R, which may be the same or different, represents a hydrocarbyl group.

7. A process according to claim 1 in which the inorganic particulate material is selected from γ-alumina, aluminium phosphate and zirconium phosphate.

8. A process according to claim 2 in which the nickel compound is selected from π-crotyl nickel methyl tricyclohexylphosphine; π-crotyl nickel methyl triphenylphosphine; π-allyl nickel benzyltricyclohexylphosphine; π-crotyl nickel methyl tri-isopropylphosphine; bis π-allyl nickel; π-allyl nickel methyl tricyclohexylphosphine; and π-crotyl nickel methyl.

9. A process according to claim 1 which is carried out at a temperature in the range 10° to 70° C and a pressure in the range 20 to 50 bars.

10. A mixture of ethylene oligomers prepared by a process according to claim 1.

11. A mixture of ethylene oligomers according to claim 10 of which >80% are α-olefins and >80% of said α-olefins have a molecular weight of ≯ 112.

* * * * *